United States Patent [19]

Walther et al.

[11] Patent Number: 4,992,732
[45] Date of Patent: Feb. 12, 1991

[54] METHOD AND APPARATUS FOR MAGNETIC TESTING OF METALLIC WORK PIECES

[75] Inventors: Karl G. Walther, Schwerte; Ronald G. Walther, Aachen, both of Fed. Rep. of Germany

[73] Assignee: Magfoil & It GmbH, Fed. Rep. of Germany

[21] Appl. No.: 345,762

[22] Filed: May 1, 1989

Related U.S. Application Data

[63] Continuation-in-part of Ser. No. 208,137, Jun. 16, 1988, abandoned, and a continuation-in-part of Ser. No. 208,169, Jun. 16, 1988, abandoned.

[30] Foreign Application Priority Data

Jul. 8, 1987 [DE] Fed. Rep. of Germany ....... 3722569
Jul. 8, 1987 [DE] Fed. Rep. of Germany ....... 3722596

[51] Int. Cl.$^5$ .................... G01N 27/84; G01R 33/12
[52] U.S. Cl. .................................................. 324/216
[58] Field of Search ............................. 324/214–216

[56] References Cited

FOREIGN PATENT DOCUMENTS

| | | |
|---|---|---|
| 2220951 | 11/1973 | Fed. Rep. of Germany . |
| 2632965 | 1/1978 | Fed. Rep. of Germany . |
| 3145090 | 11/1983 | Fed. Rep. of Germany . |
| WO80/01417 | 12/1978 | PCT Int'l Appl. . |
| 439324 | 12/1935 | United Kingdom . |
| 1602643 | 11/1981 | United Kingdom . |

*Primary Examiner*—Walter E. Snow
*Attorney, Agent, or Firm*—Brumbaugh, Graves, Donohue & Raymond

[57] ABSTRACT

Method and apparatus for inspecting weld seams by means of particles of magnetizable material which align themselves in a magnetic field in a manner characteristic of faults the particles are suspended at the start of a test in a first liquid $Fl_1$, the particles being freely mobile in the suspension and no viscosity change of the suspension taking place. Thereafter a substance is added to the suspension which effects a change of state, the particles aligned in the magnetic field thereby being fixed in their position.

13 Claims, 2 Drawing Sheets

METHOD AND APPARATUS FOR MAGNETIC TESTING OF METALLIC WORK PIECES

BACKGROUND OF THE INVENTION

This application is a continuation-in-part of U.S. Application Ser. No. 208,137 and U.S. Application Ser. No. 208,169 both filed June 16, 1988 and now abandoned.

The present invention relates to a method of testing metallic workpieces, in particular weld seams, in which particles of magnetizable material are mixed in an at least partially transparent container with a liquid and arranged near the point of the workpiece to be tested, a magnetic field is generated at the point to be tested and in the particle/liquid mixture, the path of said field is influenced by faults in the workpiece and the particles arrange themselves in a characteristic manner in the presence of faults, and the particles/liquid mixture changes its state after a period of time in such a manner that the particles oriented by the magnetic field are fixed in their position in the container.

The present invention also relates to an apparatus for testing metallic workpieces, especially weld seams, comprising a container having a support sheet and a viewing sheet between which particles of magnetizable material can be suspended in a liquid, and in a magnetic field passing through the workpiece to be tested the suspended particles arrange themselves in characteristic manner in the presence of faults.

Such a method and an apparatus are described in DE-PS 3,145,090 and serve in particular to find faults or defects in weld seams under water. In the known apparatus a main chamber having two subchambers is formed on a support sheet. In one subchamber is a mixture of various pulverulent substances including magnetizable particles (e.g. iron powder) while in the other subchamber a liquid is contained. The main chamber is formed substantially by a transparent sheet or foil (viewing sheet) and placed under water on the workpiece to be inspected, the viewing sheet pointing towards the workpiece with the support sheet remote from the workpiece. After the main chamber has been placed on the workpiece to be inspected (i.e. for example the weld seam) the two subchambers are broken open mechanically by pressure so that their content mixes in the main chamber. The magnetizable particles are thereby mixed with the other pulverulent constituents into the liquid and a magnetic field is applied which passes through the point or area of the workpiece to be investigated and through the mixture of particles and liquid. The path of the magnetic field is influenced by any faults which may be present in the workpiece (e.g. cracks in the weld seam) and the particles of magnetizable material arrange themselves in the magnetic field in a manner characteristic of the fault.

According to DE-PS 3,145,090 after about one minute a change of state occurs in the particles/liquid mixture in such a manner that the particles of magnetizable material are fixed in their location so that the arrangement characteristic of a fault is retained even after switching off the magnetic field and removing the container from the workpiece to be tested. The container is then removed by the diver and taken to the surface where the fixed arrangement of the particles is investigated and deductions made on the flaws in the workpiece.

In the known method the change of state in the particles/liquid mixture takes place at a predetermined time after the breaking open of the two subchambers and the suspending of the pulverulent constituents in the liquid. During this time the diver must carry out a great number of operations, particularly securing the container to the point of the workpiece to be investigated and positioning of the magnetizing device. If the diver does not succeed in carrying out all the operations with the necessary accuracy in the predetermined time the change of state in the particles/liquid mixture takes place too early and the measurement result is useless.

The time however which a diver needs to carry out the above operations depends on the conditions, for example visibility, current conditions under the water, accessibility of the workpiece, and so forth.

In the method described in DE-PS No. 3,145,090 the time to the start of the change of state of the particles/liquid mixture can also optionally be set within a narrow range when making the containers. The time delay to the start of the change of state (solidification) is controlled by the amount of methyl cellulose admixed. If the delay is to be increased the amount of methyl cellulose must be increased. However, this influences in a disadvantageous manner the viscosity of the mixture; i.e., the mixture becomes more viscous. Increasing the viscosity of the mixture has the disadvantageous effect that the mobility of the particles of magnetizable material is reduced. The movement of the particles due to the magnetic field in the mixture is therefore obstructed so that the characteristic arrangement of the particles caused by the faults can also be impaired. It is desirable that the particles have the highest possible mobility in the liquid in the phase in which they align and arrange themselves in the magnetic field.

In the known method, the time to silicification of the particles/liquid mixture depends on the hygroscopy of the methyl cellulose and can be adjusted to about 30 to 90 seconds. Increasing the proportion of methyl cellulose also results in the silicification process taking place relatively slowly. The mixture is adjusted so that about 5 minutes after mixing of the substances from the two subchambers a solidity is obtained and the container can be removed from the workpiece and carried away. The final solidity of the mixture is not achieved until after about three hours. It is desirable to shorten this time.

As explained above it is desirable in the actual measuring phase in which the particles arrange themselves in the magnetic field in a manner characteristic of the faults to have the highest possible mobility of the particles in the suspension. This is particularly important in working "overhead" because then the magnetic forces must counteract the force of gravity on the particles. For this reason, in the known method lead oxide is added to the powder mixture to give the carbonyl iron additional lift. However, the lead oxide reduces the contrast in the particle image produced so that the evaluation of the images is made more difficult. The claimed invention therefore is based on the problem of further developing a method for testing metallic workpieces in such a manner that is easier to carry out. In particular, a diver is not to be bound to predetermined periods of time for carrying out the inspection work.

The weld seams to be investigated do not as a rule run rectilinearly but are curved so that the flat containers placed against the weld seams after the change of state (viscosity change or silicification) are also curved. In the prior art it is necessary to leave the containers in a curved state and effect the evaluation in this condition. A flattening of the containers after removal from the weld seam inspected usually results in destruction or at least impairment of the characteristic arrangement of the particles.

Thus, with the known apparatus the structures of the particles typical of the faults had to be copied on paper and it was necessary to photograph the curved containers with a camera and make paper prints from the exposures.

The claimed invention therefore is also based on the problem of further developing an apparatus for inspecting metallic workpieces in such a manner that with simple production a reliable and certain evaluation of the test results is possible.

SUMMARY OF THE INVENTION

The claimed invention relates to a method of testing metallic workpieces, which comprises
at the start of a test the particles of magnetizable material are already suspended or are then suspended in a first liquid ($Fl_1$), no change of state fixing the position of the particles yet taking place in the particle/liquid mixture, and that particles in the magnetic field arrange themselves in the manner characteristic of faults;
that thereafter in the container at a freely selectable point of time there is added to the particles/liquid mixture a substance ($Fl_2$) which effects the change of state or condition in the mixture and fixing of the orientated particles.

The claimed invention also provides an apparatus for testing metallic workpieces by means of particles of magnetizable material which are aligned in a magnetic field, a first liquid being contained in a first chamber which is miscible with a powder containing the particles, without undergoing a change of state fixing the particles in their position, and in a second chamber a further substance being contained which on addition to the mixture of the particles and the liquid effects a change of state in the mixture securing the particles in their position. Such an apparatus may be simply and economically made in that the chambers are formed in hoses.

DETAILED DESCRIPTION OF THE INVENTION

Figure 1:
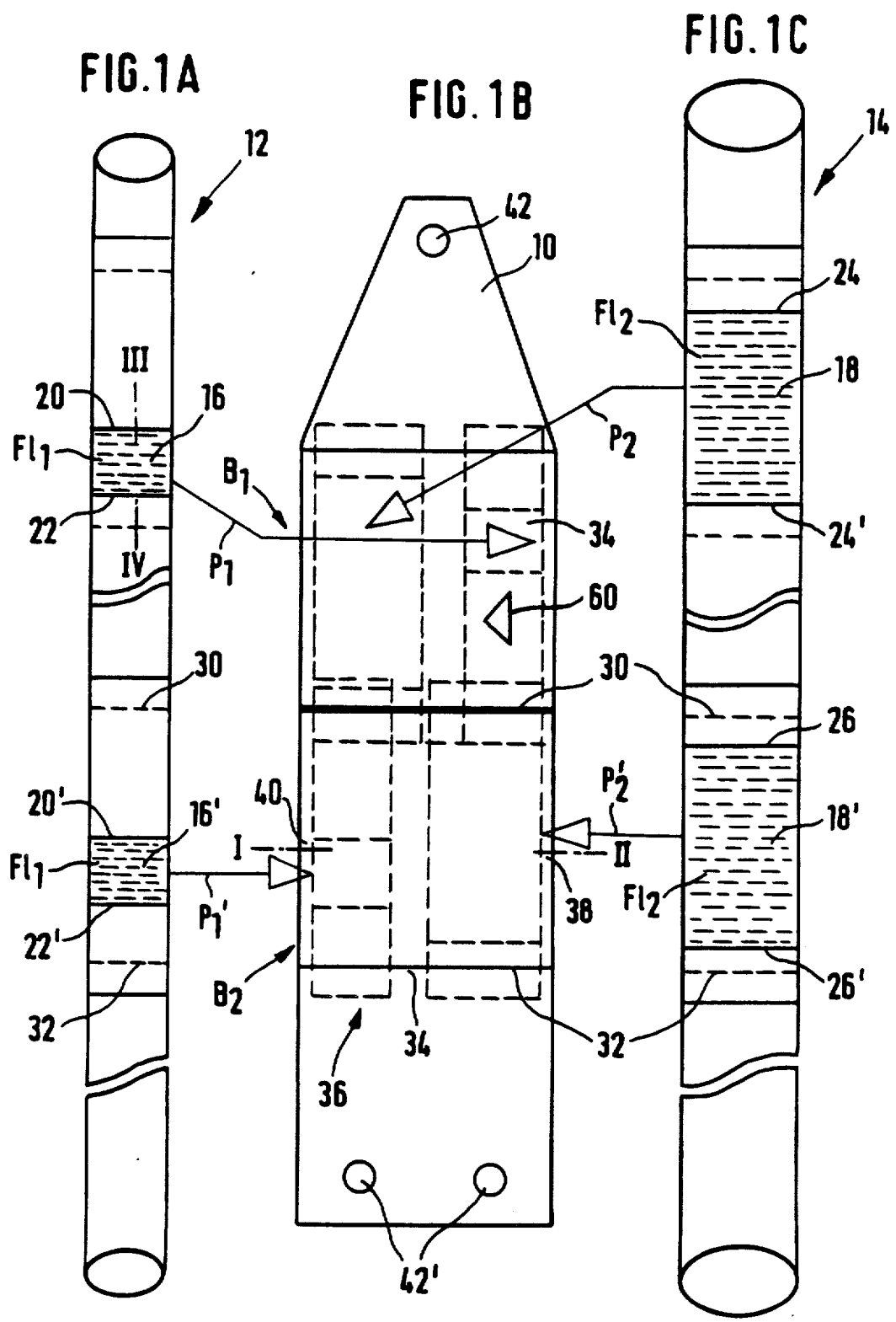
FIG. 1a, 1b and 1c are a schematic view of an apparatus for testing or inspecting metallic workpieces.

In accordance with the claimed invention, when testing material under water a diver can firstly suspend the particles of magnetizable material in a liquid in the container and he has practically any desired length of time for positioning the container on the workpiece to be tested, attaching the magnetizing device, and so forth, since no change of state has yet occurred in the suspension. Only when all the operations have been carried out does the diver mechanically or by other means, e.g. electrically heated wire, embodied in the container, break in the container a further chamber holding another substance, such as another liquid, which mixes with the suspension and causes therein a change of state on the basis of which the particles are fixed in their position produced by the magnetic field.

Preferably, the change of state of the mixture for fixing the particles is a change of the viscosity of the mixture or a silicification.

Preferably deionized water is used as the liquid in which the particles of magnetizable material can be suspended without appreciable change of state, and a second liquid, such as an alkaline solution of nesosilicates, is used as the added substance for the change of state.

The particles of magnetizable material are preferably contained in a powder mixture which also includes zinc oxide and white cement but no methyl cellulose. In the deionized water the particles of magnetizable material first have a high mobility so that they rapidly align themselves in the magnetic field. As a rule a magnetizing time of 20 seconds suffices. If then the alkaline solution of nesosilicates is mixed into the suspension a silicification first starts relatively slowly at a few nuclei. The silicification then rapidly increases until the particles are fixed.

Whereas in the prior art, DE-PS No. 3,145,090, the effectiveness of the alkaline solution of nesosilicates in the mixture with non-deionized water diminishes after about two to three months storage time and the curing times are thereby increased. In the apparatus according to the claimed invention, the liquid, such as deionized water, and the substance causing the change of state, such as an alkaline solution of nesosilicates, are kept separately in the container so that the shelf life is substantially increased.

The known apparatus has the further disadvantage that in particular when working "overhead" air components from the powder mixture due to their buoyancy settle on the viewing sheet, thereby making the analysis of the structures produced by the fixed particles more difficult.

To avoid this disadvantage in a preferred further embodiment of the invention, a powder mixture containing as essential constituents white cement, carbonyl iron and zinc oxide is compacted after mixing in a mechanical press to form a lens-shaped pellet. This pellet or tablet is placed in a powder chamber provided in the container and said chamber is then evacuated in a vacuum chamber to remove the gases.

In the claimed apparatus a net is disposed between the viewing sheet and the support sheet. The net is of fine-filament plastic and assures that the particles after their orientation and collection in the magnetic field remain in the position assumed and do not change their position during the manipulation of the container following the measurement. The initially liquid suspension of the particles aligned in the magnetic field changes due to the aforementioned change of state to a largely solidified (i.e. no longer liquid) "carrier mass" for which the plastic net provided according to the invention is a support. The plastic net is resilient (e.g. a nylon stocking) and secures the particles together with the carrier mass surrounding them.

Figure 4:
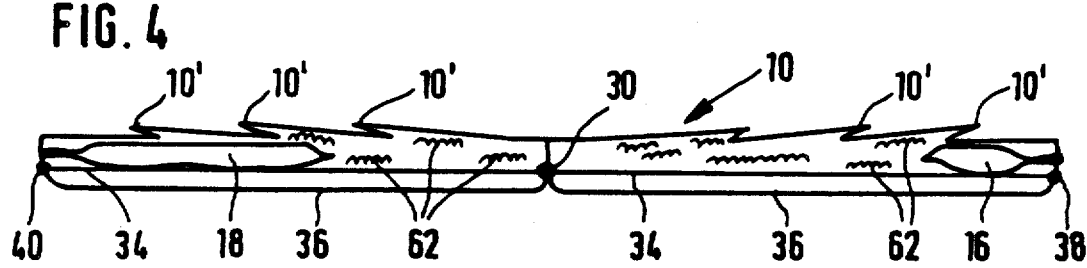
FIG. 4 shows a container according to the invention in the flat state.

The plastic net according to the invention is welded in the container just beneath the viewing or inspection sheet. It does not obstruct the evaluation of the particle image. Since the net is arranged near the viewing sheet after the test has been carried out, the main part of the solidified carrier mass lies between the net and the support sheet. In a preferred further embodiment as shown in FIG. 4 of the invention this carrier mass is stabilized at its location due to a plurality of crimped (e.g. spiral-shaped) fibers 62 added to the powder. The fibers have, for example, a length of about 25 mm and stabilize the surrounding carrier mass, against cracking and disintegrating. As shown in FIG. 4, the crimped fibers 62 are located between the net 35 and the support sheet 10.

In a preferred embodiment of the apparatus according to the invention, two chambers are arranged between the net and the support sheet, one of which contains a liquid in which the particles of magnetizable material are suspended while the other chamber contains a substance, in particular a liquid, which can be added to the suspension to effect a change of state so that the particles can no longer move away from the assumed location.

In a preferred embodiment of the invention the particles of magnetizable material compressed to form the substantially gas-free pellet are disposed between the net and the viewing sheet.

After carrying out the measurement, the container of the invention can be pressed flat between two plane-parallel plates of non-magnetic material without destroying the oriented structure of the magnetic particles. The flat pressed containers may be placed on a copier to directly image the particle structures.

Figure 3:
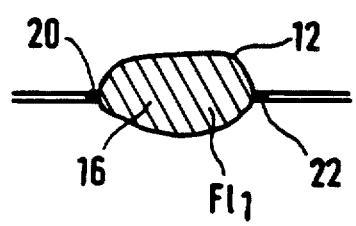
FIG. 3 is a section along the line III—IV of FIG. 1.

FIG. 1 shows a support sheet 10 of plastic and two hoses 12 and 14, likewise of plastic. In the hoses 12 and 14 on the left and right of the support sheet 10 liquid chambers 16, 16', 18, 18' are formed (see also FIG. 3). By welded or adhered seams 20, 20', 22, 22', 24, 24', 26 and 26' the individual chambers are separated in the two hoses 12 and 14 respectively.

A liquid $Fl_1$ is contained in each of the chambers 16, 16'. In the embodiment illustrated the liquid $Fl_1$ is deionized water. In the chambers 18, 18' an alkaline solution of nesosilicates is contained.

In the production of the ready-to-use apparatus for testing metallic workpieces, the chambers 16, 16', 18, 18' formed in the hoses 12 and 14 are positioned in accordance with the arrows $P_{1'}$ $P_{1'}$, $P_2$ and $P_{2'}$, on the support sheet 10.

Figure 2:
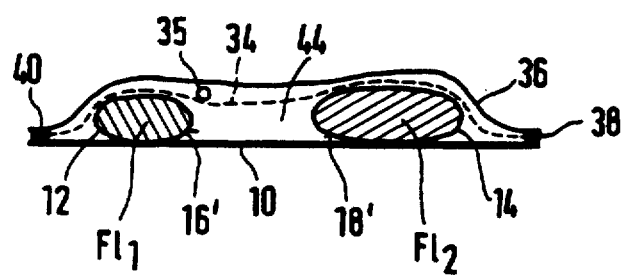
FIG. 2 a section along the line I—II of FIG. 1.

In accordance with FIGS. 1 and 2 a continuous net of plastic is placed over the chambers 16, 16', 18, 18' arranged on the support sheet 10 and over the net a transparent viewing sheet 36, also of plastic, is placed. Then, in accordance with FIGS. 1 and 2 the support sheet 10, the net 34 and the viewing or inspection sheet 36 are joined together along the weld seams 38 and 40. The chambers 16, 16', 18, and 18' are also joined by welding or adhering at projecting hose portions to the support sheet 10.

Furthermore, between the viewing sheet 36 and the net 34 adjacent the chambers 16, 16' containing the deionized water, in each case compressed and evacuated pellets of a powder containing carbonyl iron, zinc oxide, white cement (not shown) are arranged.

According to FIG. 1 on the support sheet 10 two containers, $B_1$ and $B_2$, are formed which are separated by the weld seam 30 and each contain a chamber with the liquid $Fl_1$, a chamber with the liquid $Fl_2$, and the pellet.

As apparent from FIG. 1 in the two adjacent containers, $B_1$ and $B_2$, separated by the weld seam 30 the chambers with the different liquids $Fl_1$ and $Fl_2$, are arranged "crosswise", i.e. in the upper container $B_1$ the chamber 18 is arranged on the left according to the arrow $P_2$, and the chamber 16 on the right according to the arrow $P_1$, while in the container $B_2$ beneath the weld seam 30 the chambers 16' and 18' are arranged on the left and right in accordance with the arrows $P_{1'}$ and $P_{2'}$, respectively.

For carrying out the test of a weld seam for cracks or other faults the support sheet is placed by the diver under water onto the weld seam to be investigated in such a manner that the viewing sheet 36 lies directly on the weld seam, i.e. the support sheet 10 is remote from the weld seam. The diver has previously caused the chambers 16, 16' containing deionized water $Fl_1$ to burst mechanically by applying pressure so that in the main chamber 44 (FIG. 2) formed between the support sheet 10 and the viewing sheet 36 the powder pellet 35 dissolves in the deionized water.

The diver then places a magnetizing device in a manner known per se on the workpiece to be tested so that a magnetic field passes both through the weld seam to be investigated and the suspension of the particles of magnetizable material (in this case carbonyl iron). The particles orient themselves in the magnetic field and form characteristic structures at faults, for example grooves, accumulations, etc., which can be subsequently analyzed by an expert.

Since no viscosity change yet occurs in the suspension of deionized water and the powder mixture containing zinc oxide, white cement and carbonyl iron, the powder particles are freely mobile and can align themselves in the magnetic field very rapidly, for example within 1 second. On attaching the support sheet over the weld seam and on positioning the magnetic device the diver is not subjected to any time restrictions whatever. Only when these operations have been concluded does the diver open the chambers 18, 18' by pressure or other means, for example by electrically heated wire inside the container, so that the liquid $Fl_2$, i.e. the alkaline solution of nesosilicates, penetrates into the suspension and causes a change of state on the basis of which the aligned particles of magnetizable material are fixed in their position characteristic of any faults present.

The plastic net 34 promotes the fixation of the particles so that after the change of state in the suspension (in this case a silicification) the support sheet 10 can be removed from the investigated weld seam and brought on deck without the characteristic arrangement of the particles being destroyed.

We claim:

1. An apparatus for testing metallic workpieces which comprises:
   a support sheet and a transparent viewing foil attached to each other along their perimeters;
   a net disposed between the support sheet and the viewing foil;
   at least one openable first chamber containing a fluid and disposed between the support sheet and the viewing foil;
   at least one openable second chamber containing a substance and disposed between the support sheet and the viewing foil; and
   particles of magnetizable material disposed between the support sheet and the viewing foil, said particles of magnetizable material being mobile when dispersed in the fluid and immobile when dispersed in both the fluid and the substance.

2. The apparatus according to claim 1, wherein the first chamber, the second chamber and the particles of magnetizable material are disposed between the support sheet and the net.

3. The apparatus according to claim 1, wherein the first chamber, the second chamber and the particles of magnetizable material are disposed between the net and the viewing foil.

4. The apparatus according to claim 1, wherein the substance, when in contact with the fluid, effects a viscosity change.

5. The apparatus according to claim 1 wherein the particles of magnetizable material are in the form of a compression molded pellet before dispersion in the fluid or the substance.

6. The apparatus according to claim 1, further comprising a plurality of spiral-shaped fibers between the support sheet and the viewing foil.

7. The apparatus according to claim 1, further comprising a plurality of spiral-shaped fibers between the support sheet and the net.

8. The apparatus according to claim 1, wherein the net comprises fine-filament plastic.

9. The apparatus according to claim 1, comprising at least two first chambers arranged diagonally from one another between the support sheet and the net and at least two second chambers also arranged diagonally from one another between the support sheet and the net.

10. The apparatus according to claim 1, wherein the support sheet comprises different markings at its ends.

11. The apparatus according to claim 1, wherein the first and second chambers are located within hoses.

12. The apparatus according to claim 1, wherein the fluid is deionized water.

13. The apparatus according to claim 1, wherein the substance is an alkaline solution of nesosilicates.

* * * * *